US012616531B2

(12) United States Patent
Schena et al.

(10) Patent No.:　　US 12,616,531 B2
(45) Date of Patent:　　　May 5, 2026

(54) MULTI-PORT SURGICAL ROBOTIC SYSTEM ARCHITECTURE

(71) Applicant: Intuitive Surgical Operations, Inc., Sunnyvale, CA (US)

(72) Inventors: Bruce Michael Schena, Menlo Park, CA (US); Roman L. Devengenzo, San Jose, CA (US); Scott Luke, Ben Lomond, CA (US); David Martin, Santa Clara, CA (US); Thomas G. Cooper, Menlo Park, CA (US); Thomas Brown, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 17/591,196

(22) Filed: Feb. 2, 2022

(65) Prior Publication Data

US 2022/0151715 A1　　May 19, 2022

Related U.S. Application Data

(63) Continuation of application No. 16/741,917, filed on Jan. 14, 2020, now Pat. No. 11,576,734, which is a
(Continued)

(51) Int. Cl.
*A61B 34/30*　　　　(2016.01)
*A61B 17/00*　　　　(2006.01)
(Continued)

(52) U.S. Cl.
CPC .............. *A61B 34/30* (2016.02); *A61B 34/37* (2016.02); *F16M 11/2035* (2013.01);
(Continued)

(58) Field of Classification Search
CPC ......... A61B 34/30; A61B 34/37; A61B 34/35; A61B 2034/304; A61B 90/50; A61B 2090/506
See application file for complete search history.

(56) References Cited

U.S. PATENT DOCUMENTS 5,184,601 A　2/1993　Putman
5,445,166 A　8/1995　Taylor et al.
(Continued)

FOREIGN PATENT DOCUMENTS

CN　　　101919736 A　12/2010
JP　　　2001275931 A　10/2001
(Continued)

OTHER PUBLICATIONS

Extended European Search Report for Application No. EP22174713.2, mailed on Sep. 9, 2022 6 pages.
(Continued)

*Primary Examiner* — Katherine M Shi
*Assistant Examiner* — Mohammed S Adam
(74) *Attorney, Agent, or Firm* — Jones Burke, PLLC

(57) ABSTRACT

A robotic surgery system includes a mounting base, a column base fixedly coupled with the mounting base, a translatable column member slideably coupled to the column base, an orienting platform coupled with the translatable column member, outer set-up linkages, and outer surgical instrument manipulators. Each of the outer set-up linkages is rotationally coupled to and supported by the orienting platform. Each of the outer set-up linkages includes an extension link, a coupling link, and a first joint that couples the respective coupling link to the respective extension link. Each of the outer surgical instrument manipulators is operable to selectively articulate a respective surgical instrument mounted to the outer surgical instrument
(Continued)

manipulator and to insert the surgical instrument along an insertion axis through a remote center of manipulation.

17 Claims, 15 Drawing Sheets

Related U.S. Application Data continuation of application No. 15/156,231, filed on May 16, 2016, now Pat. No. 10,575,908, which is a continuation of application No. 13/907,009, filed on May 31, 2013, now Pat. No. 9,358,074.

(60) Provisional application No. 61/654,367, filed on Jun. 1, 2012.

(51) Int. Cl.
|  |  |
|---|---|
| *A61B 34/35* | (2016.01) |
| *A61B 34/37* | (2016.01) |
| *F16M 11/20* | (2006.01) |

(52) U.S. Cl.
CPC ............... *A61B 2017/00477* (2013.01); *A61B 2034/304* (2016.02); *A61B 34/35* (2016.02)

(56) References Cited

U.S. PATENT DOCUMENTS

| | | | |
|---|---|---|---|
| 5,800,423 A | 9/1998 | Jensen et al. | |
| 5,808,665 A | 9/1998 | Green et al. | |
| 5,855,583 A | 1/1999 | Wang et al. | |
| 5,976,156 A | 11/1999 | Taylor et al. | |
| 6,246,200 B1 | 6/2001 | Blumenkranz et al. | |
| 6,331,181 B1 | 12/2001 | Tierney et al. | |
| 6,676,669 B2 | 1/2004 | Charles et al. | |
| 6,702,805 B1 | 3/2004 | Stuart et al. | |
| 6,758,843 B2 | 7/2004 | Jensen et al. | |
| 6,788,018 B1 | 9/2004 | Blumenkranz | |
| 6,936,042 B2 | 8/2005 | Wallace et al. | |
| 7,594,912 B2 | 9/2009 | Cooper et al. | |
| 7,763,015 B2 | 7/2010 | Cooper et al. | |
| 8,004,229 B2 | 8/2011 | Nowlin et al. | |
| 8,162,926 B2 | 4/2012 | Schena | |
| 9,358,074 B2 | 6/2016 | Schena et al. | |
| 9,358,682 B2 | 6/2016 | Ruiz Morales | |
| 10,575,908 B2 | 3/2020 | Schena et al. | |
| 2001/0013764 A1 | 8/2001 | Blumenkranz et al. | |
| 2003/0208189 A1 | 11/2003 | Payman | |
| 2004/0263102 A1* | 12/2004 | Kraus ................. | F16M 11/105 |
| | | | 318/432 |
| 2006/0074406 A1* | 4/2006 | Cooper ................. | A61B 34/37 |
| | | | 606/1 |
| 2006/0142738 A1 | 6/2006 | Dohi et al. | |
| 2007/0138992 A1 | 6/2007 | Prisco et al. | |
| 2007/0156122 A1 | 7/2007 | Cooper | |
| 2007/0173977 A1 | 7/2007 | Schena | |
| 2009/0041565 A1 | 2/2009 | Rodriguez | |
| 2009/0048611 A1 | 2/2009 | Funda et al. | |
| 2009/0163931 A1 | 6/2009 | Cooper et al. | |

| | | | |
|---|---|---|---|
| 2010/0204713 A1* | 8/2010 | Ruiz Morales .......... | B25J 9/041 |
| | | | 606/130 |
| 2010/0262162 A1 | 10/2010 | Omori | |
| 2011/0288561 A1 | 11/2011 | Devengenzo et al. | |
| 2012/0088963 A1 | 4/2012 | Yasunaga et al. | |
| 2012/0267497 A1 | 10/2012 | Bowman et al. | |
| 2014/0052153 A1 | 2/2014 | Griffiths et al. | |
| 2014/0052154 A1 | 2/2014 | Griffiths et al. | |
| 2015/0257840 A1 | 9/2015 | Mohr et al. | |
| 2020/0146759 A1 | 5/2020 | Schena et al. | |
| 2022/0175476 A1 | 6/2022 | Schena et al. | |

FOREIGN PATENT DOCUMENTS

| | | | |
|---|---|---|---|
| JP | 2002103255 A | 4/2002 |
| JP | 2003053684 A | 2/2003 |
| JP | 2003299674 A | 10/2003 |
| JP | 2005013715 A | 1/2005 |
| JP | 2005516786 A | 6/2005 |
| JP | 4131731 B2 | 8/2008 |
| JP | 2009106738 A | 5/2009 |
| JP | 2009160011 A | 7/2009 |
| JP | 2010524547 A | 7/2010 |
| JP | 2011520489 A | 7/2011 |
| JP | 2012095679 A | 5/2012 |
| KR | 20090089928 A | 8/2009 |
| KR | 100974464 B1 | 8/2010 |
| KR | 20120014758 A | 2/2012 |
| WO | WO-9507055 A1 | 3/1995 |
| WO | WO-2004035270 A1 | 4/2004 |
| WO | WO-2006039092 A2 | 4/2006 |
| WO | WO-2006079108 A1 | 7/2006 |
| WO | WO-2006124390 A2 | 11/2006 |
| WO | WO-2007045810 A2 | 4/2007 |
| WO | WO-2007088206 A2 | 8/2007 |
| WO | WO-2007114975 A2 | 10/2007 |
| WO | WO-2009104853 A1 | 8/2009 |
| WO | WO-2010044536 A1 | 4/2010 |
| WO | WO-2010068005 A2 | 6/2010 |
| WO | WO-2011060046 A2 | 5/2011 |
| WO | WO-2011143023 A1 | 11/2011 |
| WO | WO-2011143024 A1 | 11/2011 |
| WO | WO-2011149187 A2 | 12/2011 |
| WO | WO-2011149260 A2 | 12/2011 |
| WO | WO-2011155411 A1 | 12/2011 |
| WO | WO-2013078529 A1 | 6/2013 |
| WO | WO-2013181533 A1 | 12/2013 |

OTHER PUBLICATIONS

Extended European Search Report for Application No. 13798217.9, mailed on May 17, 2016, 15 pages.
Extended European Search Report for Application No. 19204702.5 mailed on Jan. 23, 2020, 12 pages.
International Search Report and Written Opinion for Application No. PCT/US2013/043612, mailed on Sep. 5, 2013, 14 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

60 — DISPLAY

50

52 — SURGEON'S CONSOLE

58 — PROCESSOR

54 — PATIENT SIDE CART (SURGICAL ROBOT)

56 — ELECTRONICS CART

62

MULTI-PORT SURGICAL ROBOTIC SYSTEM ARCHITECTURE

CROSS-REFERENCES TO RELATED APPLICATIONS

The present application is a Continuation of U.S. patent application Ser. No. 16/741,917 filed Jan. 14, 2020 (published as US 2020-0146759); which is a Continuation of U.S. patent application Ser. No. 15/156,231 filed May 16, 2016 (now U.S. Pat. No. 10,575,908); which is a Continuation of U.S. patent application Ser. No. 13/907,009 filed May 31, 2013 (now U.S. Pat. No. 9,358,074); which claims the benefit of U.S. Provisional Appln No. 61/654,367 filed Jun. 1, 2012; the full disclosures which are incorporated herein by reference in their entirety for all purposes.

BACKGROUND

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive robotic surgical or telesurgical systems have been developed to increase a surgeon's dexterity and avoid some of the limitations on traditional minimally invasive techniques. In telesurgery, the surgeon uses some form of remote control (e.g., a servomechanism or the like) to manipulate surgical instrument movements, rather than directly holding and moving the instruments by hand. In telesurgery systems, the surgeon can be provided with an image of the surgical site at a surgical workstation. While viewing a two or three dimensional image of the surgical site on a display, the surgeon performs the surgical procedures on the patient by manipulating master control devices, which in turn control motion of the servo-mechanically operated instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a robotic surgical system is the DA VINCI® system available from Intuitive Surgical, Inc. of Sunnyvale, Calif.

A variety of structural arrangements can be used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 7,594,912; 6,758,843; 6,246,200; and 5,800, 423; the full disclosures of which are incorporated herein by reference. These linkages often make use of a parallelogram arrangement to hold an instrument having a shaft. Such a manipulator structure can constrain movement of the instrument so that the instrument pivots about a remote center of manipulation positioned in space along the length of the rigid shaft. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 7,763,015; 6,702,805; 6,676, 669; 5,855,583; 5,808,665; 5,445,166; and 5,184,601; the full disclosures of which are incorporated herein by reference.

A variety of structural arrangements can also be used to support and position the robotic surgical manipulator and the surgical instrument at the surgical site during robotic surgery. Supporting linkage mechanisms, sometimes referred to as set-up joints, or set-up joint arms, are often used to position and align each manipulator with the respective incision point in a patient's body. The supporting linkage mechanism facilitates the alignment of a surgical manipulator with a desired surgical incision point and targeted anatomy. Exemplary supporting linkage mechanisms are described in U.S. Pat. Nos. 6,246,200 and 6,788,018, the full disclosures of which are incorporated herein by reference.

While the new telesurgical systems and devices have proven highly effective and advantageous, still further improvements are desirable. In general, improved minimally invasive robotic surgery systems are desirable. It would be particularly beneficial if these improved technologies enhanced the efficiency and ease of use of robotic surgical systems. For example, it would be particularly beneficial to increase maneuverability, improve space utilization in an operating room, provide a faster and easier set-up, inhibit collisions between robotic devices during use, and/or reduce the mechanical complexity and size of these new surgical systems.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Improved robotic surgery systems and modular manipulator supports for use in robotic surgery systems are disclosed. An improved robotic surgery system includes an orienting platform that is used to support a plurality of set-up linkages, each of which supports an associated surgical instrument manipulator, or manipulators. A support linkage is used to movably support the orienting platform. One or more of the support linkages can include a reorientation mechanism operable to reposition the manipulator via a motion that maintains an associated remote center of manipulation (RC) in a fixed position, thereby allowing the supported manipulator to be repositioned without the risk of inducing potentially dangerous forces to a patient at an incision location. And one or more of the support linkages can also include a first link rotationally coupled to the orienting platform, a second link slideably mounted to the first link to slide horizontally relative to the first link, a third link slideably mounted to the second link to slide vertically relative to the second link, and a fourth link rotationally coupled to the third link to rotate relative to the third link about a vertical axis. The support linkage can include a movable floor-supported mounting base, and an adjustable linkage coupled to the mounting base and movably support-ing the orienting platform. The mounting base can also be immovable, for example, by being attached directly to a floor or other fixed structure. The disclosed robotic surgery systems and modular manipulator supports increase maneu-verability, improve space utilization in an operating room, provide a faster and easier set-up, inhibit collisions between robotic devices during use, and have reduced mechanical complexity relative to existing systems and supports having comparable capabilities.

Thus, in one aspect, a robotic surgery system is disclosed that includes an orienting platform, a support linkage mov-ably supporting the orienting platform, a plurality of manipulators, and a plurality of set-up linkages. Each of the manipulators can include an instrument holder. Each of the manipulators can be configured to support an associated surgical instrument mounted to the instrument holder, insert the associated surgical instrument along an insertion axis into a patient through an associated remote center of manipulation (RC), rotate the instrument holder around a first manipulator axis that intersects the associated RC, and rotate the instrument holder around a second manipulator axis that intersects the associated RC. Each of the first and second manipulator axes is transverse to the insertion axis. The second manipulator axis is transverse to the first manipulator axis. Each of the set-up linkages couples one of the manipulators to the orienting platform and is operable to reposition the associated manipulator relative to the orient-ing platform and fixedly support the associated manipulator in a selected position relative to the orienting platform. Each of the set-up linkages includes a proximal link coupled to the orienting platform and a distal link coupled to the associated manipulator. At least one of the set-up linkages includes a reorientation mechanism that when actuated moves the distal link relative to the proximal link through a motion that maintains the associated RC in a fixed position relative to the proximal link.

In many embodiments, the reorientation mechanism includes a tornado rotational joint and a tornado link. The tornado link has a tornado link proximal end coupled to the tornado rotational joint and a tornado link distal end coupled to the associated manipulator. Actuation of the tornado rotational joint rotates the tornado link around a tornado axis that intersects the RC and that is not aligned with either of the first and second manipulator axes. The tornado link is configured to maintain the associated RC in a fixed position relative to the proximal link for all orientations of the tornado link around the tornado axis.

In many embodiments, at least one of the manipulators is mechanically constrained to maintain a fixed position of the associated RC relative to the distal link during the rotation of the instrument holder around the first manipulator axis and during the rotation of the instrument holder around the second manipulator axis. For example, at least one of the manipulators can be mechanically configured to move the instrument holder in response to actuation of a first joint of the manipulator through a first motion that is mechanically limited to rotation around the first manipulator axis and to move the instrument holder in response to actuation of a second joint of the manipulator through a second motion that is mechanically limited to rotation around the second manipulator axis.

In many embodiments, the support linkage includes a movable floor-supported mounting base, a column slideably mounted to the mounting base, a boom base member rota-tionally coupled to the column through a shoulder joint; and an extendable boom member slideably coupled with the boom base member through a boom joint. The column is selectively positionable relative to the mounting base along a first support axis that is vertically oriented. The shoulder joint is operable to selectively orient the boom base member relative to the column around a second support axis that is vertically oriented. The boom joint is operable to selectively position the extendable boom member relative to the boom base member along a third support axis that is horizontally oriented. The orienting platform is rotationally coupled to the extendable boom member.

In another aspect, a robotic surgery system is disclosed that includes an orienting platform, a support linkage mov-ably supporting the orienting platform, a plurality of manipulators, and a plurality of set-up linkages. Each of the manipulators movably supports an associated surgical instrument insertable into a patient. Each of the set-up linkages couples one of the manipulators to the orienting platform and is operable to reposition the associated linkage relative to the orienting platform and fixedly support the associated manipulator relative to the orienting platform. At least one of the set-up linkages includes a first link, a second link, a third link, and a fourth link. The first link has a first link proximal end rotationally coupled to the orienting platform through a first set-up linkage joint operable to selectively orient the first link relative to the orienting platform around a first set-up linkage axis. The second link is slideably mounted to the first link through a second set-up linkage joint operable to selectively reposition the second link relative to the first link along a second set-up linkage axis that is horizontally oriented. The third link is slideably mounted to the second link through a third set-up linkage joint operable to selectively reposition the third link relative to the second link along a third set-up linkage axis that is vertically oriented. The fourth link is rotationally coupled to the third link through a fourth set-up linkage joint operable to selectively orient the fourth link relative to the third link around a fourth set-up linkage axis that is substantially vertically oriented. The associated manipulator is distal to and supported by the fourth link.

In many embodiments, at least one of the manipulators can include an instrument holder configured to support the associated surgical instrument. At least one of the manipu-lators can be configured to insert the associated surgical instrument into the patient through an associated remote center of manipulation (RC), rotate the instrument holder around a first manipulator axis that intersects the associated RC, and rotate the instrument holder around a second manipulator axis that intersects the associated RC. The second manipulator axis is transverse to the first manipulator axis.

In many embodiments, at least one of the set-up linkages includes a reorientation mechanism coupled to the fourth link. Actuation of the reorientation mechanism moves the associated manipulator relative to the fourth link through a motion that maintains the associated RC in a fixed position relative to the fourth link.

In many embodiments, the reorientation mechanism includes a tornado rotational joint and a tornado link. The tornado link has a tornado link proximal end coupled to the tornado rotational joint and a tornado link distal end coupled to the associated manipulator. Actuation of the tornado rotational joint rotates the tornado link around a tornado axis that intersect the RC and that is not aligned with either of the first and second manipulator axes. The tornado link is configured to maintain the associated RC in a fixed position relative to the fourth link for all orientations of the tornado link around the tornado axis.

In another aspect, a modular manipulator support for use in a robotic surgery system is disclosed. The robotic surgery system includes a plurality of manipulators that include driven links and joints for moving an associated surgical instrument. The modular manipulator support includes a movable floor-supported mounting base, a column slideably coupled with the mounting base, a boom base member rotationally coupled to the column through a shoulder joint, an extendable boom member slideably coupled to the boom base member through a boom joint, an orienting platform rotationally coupled to the extendable boom member through a wrist joint, and a plurality of set-up linkages. The column is selectively positionable relative to the mounting base along a first support axis that is vertically oriented. The shoulder joint is operable to selectively orient the boom base member relative to the column around a second support axis that is vertically oriented. The boom joint is operable to selectively position the extendable boom member relative to the boom base member along a third support axis that is horizontally oriented. The wrist joint is operable to selectively orient the orienting platform relative to the extendable boom member around a fourth support axis that is vertically oriented. Each of the set-up linkages couples one of the manipulators to the orienting platform and is operable to selectively position the associated manipulator relative to the orienting platform and fixedly support the associated manipulator relative to the orienting platform. In many embodiments, the angular orientation of the shoulder joint is limited to prevent exceeding a predetermined stability limit of the mounting base.

In many embodiments, at least one of the set-up linkages includes a first link, a second link, a third link, and a fourth link. The first link has a first link proximal end rotationally coupled to the orienting platform through a first set-up linkage joint operable to selectively orient the first link relative to the orienting platform around a first set-up linkage axis. The second link is slideably mounted to the first link through a second set-up linkage joint operable to selectively reposition the second link relative to the first link along a second set-up linkage axis that is horizontally oriented. The third link is slideably mounted to the second link through a third set-up linkage joint operable to selectively reposition the third link relative to the second link along a third set-up linkage axis that is vertically oriented. The fourth link is rotationally coupled to the third link through a fourth set-up linkage joint operable to selectively orient the fourth link relative to the third link around a fourth set-up linkage axis that is vertically oriented. The associated manipulator is distal to and supported by the fourth link. In many embodiments, the first link is cantilevered from the first set-up linkage joint in a horizontal direction.

In many embodiments, at least one of the set-up linkages includes a reorientation mechanism coupled to and between the fourth link and the associated manipulator. Actuation of the reorientation mechanism moves the associated manipulator relative to the fourth link through a motion that maintains an associated remote center of manipulation (RC) in a fixed position relative to the fourth link.

In many embodiments, the reorientation mechanism includes a tornado rotational joint and a tornado link. The tornado link has a tornado link proximal end coupled to the tornado rotational joint and a tornado link distal end coupled to the associated manipulator. Actuation of the tornado rotational joint rotates the tornado link around a tornado axis that intersect the RC and that is not aligned with either of the first and second manipulator axes. The tornado link is configured to maintain the associated RC in a fixed position relative to the fourth link for all orientations of the tornado link around the tornado axis.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Minimally Invasive Robotic Surgery

Figure 1:
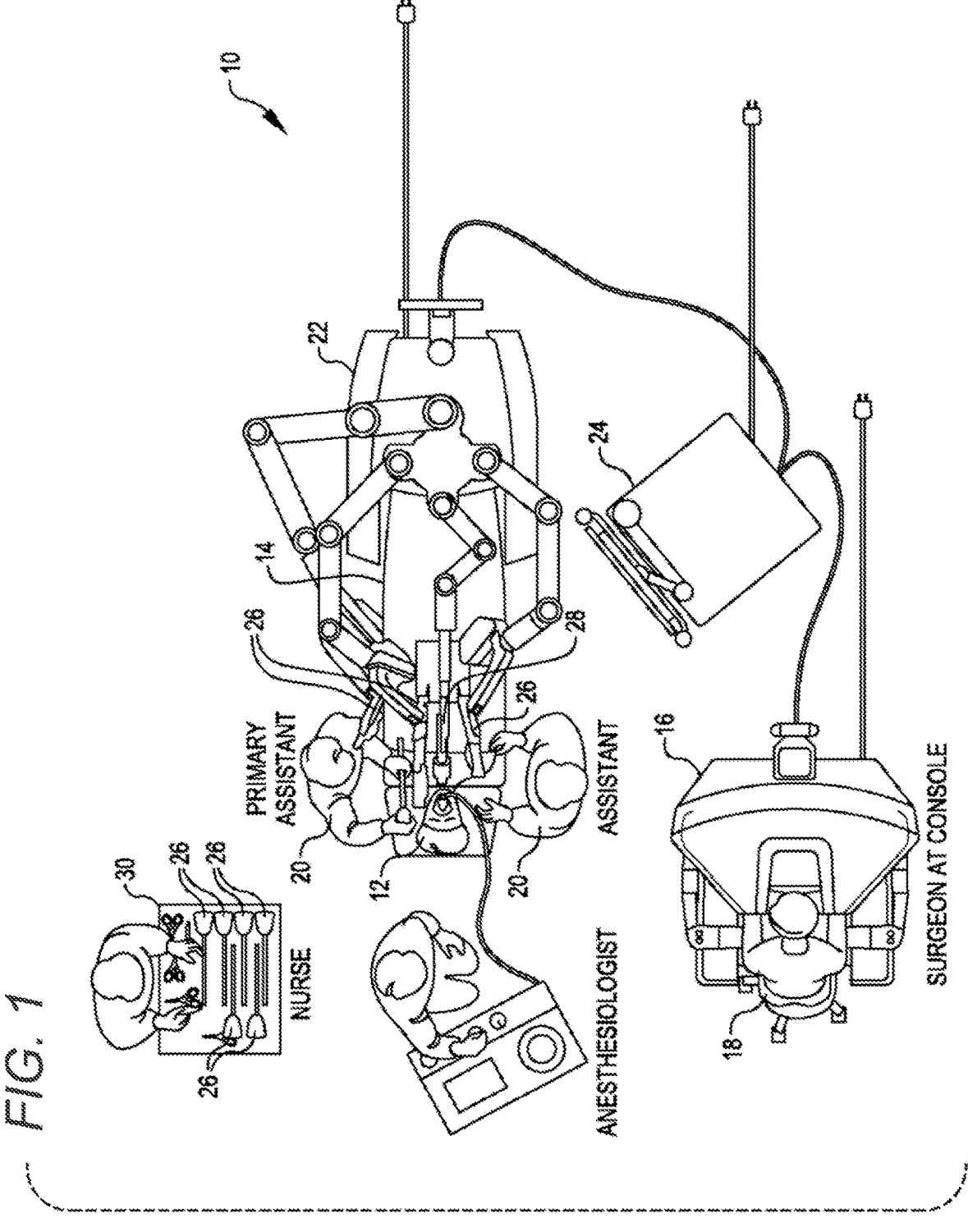
FIG. 1 is a plan view of a minimally invasive robotic surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figures 2, 3:
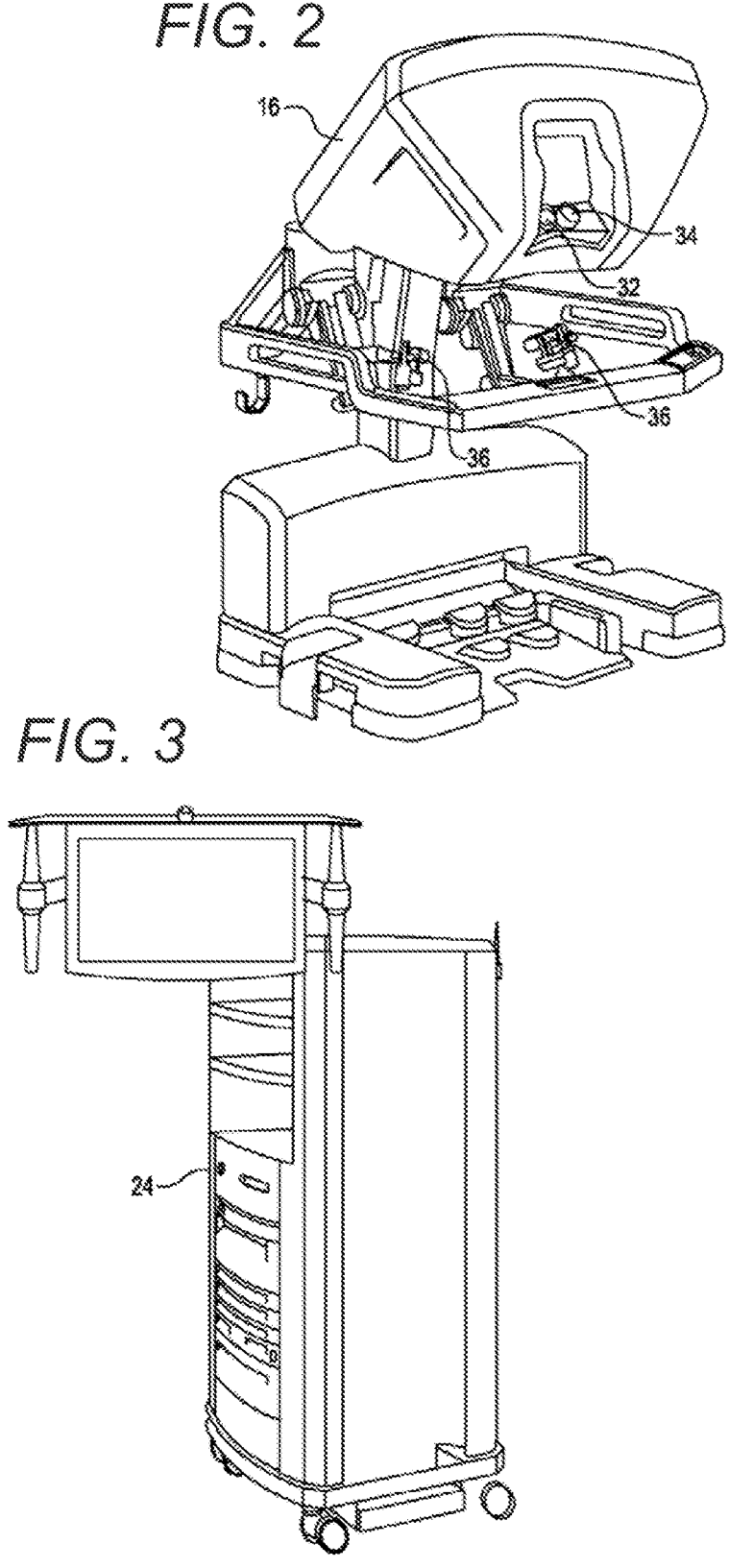
FIG. 2 is a perspective view of a surgeon's control console for a robotic surgery system, in accordance with many embodiments.
FIG. 3 is a perspective view of a robotic surgery system electronics cart, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figures 4, 5A:
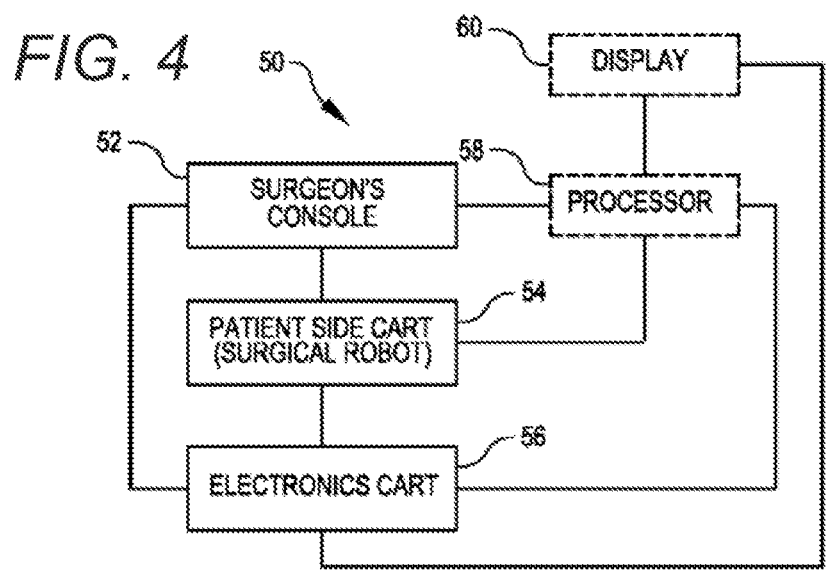
FIG. 4 diagrammatically illustrates a robotic surgery system, in accordance with many embodiments.
FIG. 5A is a partial view of a patient side cart (surgical robot) of a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5B:
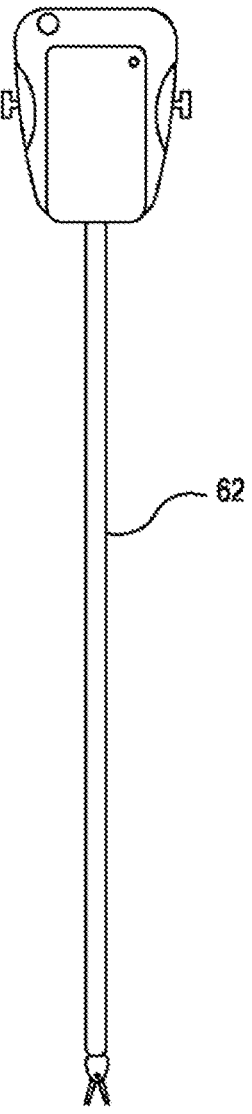
FIG. 5B is a front view of a robotic surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Robotic Surgery Systems and Modular Manipulator Supports

Figure 6:
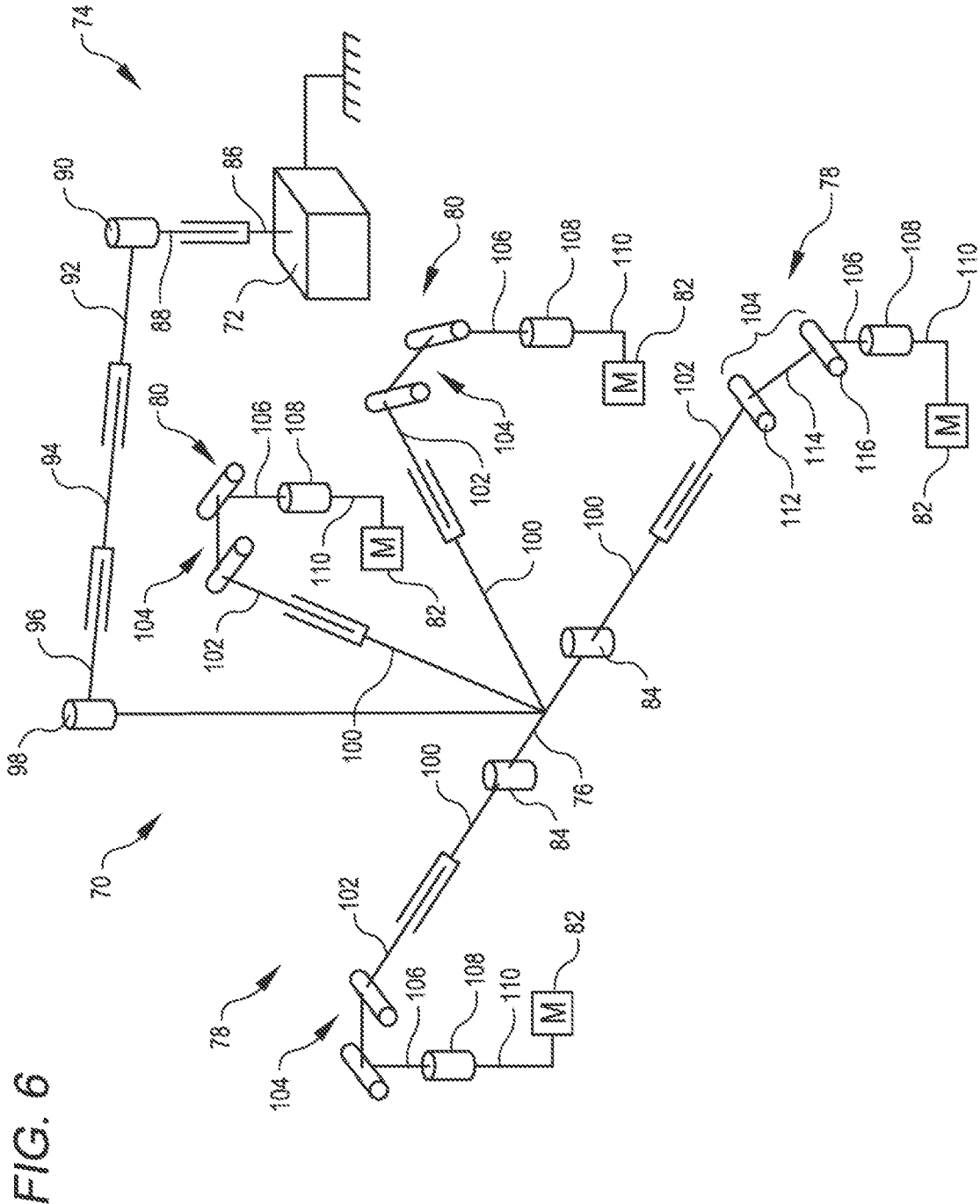
FIG. 6 is a perspective schematic representation of a robotic surgery system, in accordance with many embodiments.

FIG. 6 is a perspective schematic representation of a robotic surgery system 70, in accordance with many embodiments. The surgery system 70 includes a mounting base 72, a support linkage 74, an orienting platform 76, a plurality of outer set-up linkages 78 (two shown), a plurality of inner set-up linkages 80 (two shown), and a plurality of surgical instrument manipulators 82. Each of the manipulators 82 is operable to selectively articulate a surgical instrument mounted to the manipulator 82 and insertable into a patient along an insertion axis. Each of the manipulators 82 is attached to and supported by one of the set-up linkages 78, 80. Each of the outer set-up linkages 78 is rotationally coupled to and supported by the orienting platform 76 by a first set-up linkage joint 84. Each of the inner set-up linkages 80 is fixedly attached to and supported by the orienting platform 76. The orienting platform 76 is rotationally coupled to and supported by the support linkage 74. And the support linkage 74 is fixedly attached to and supported by the mounting base 72.

In many embodiments, the mounting base 72 is a movable and floor supported, thereby enabling selective repositioning of the overall surgery system 70, for example, within an operating room. The mounting base 72 can include a steerable wheel assembly and/or any other suitable support features that provide for both selective repositioning as well as selectively preventing movement of the mounting base 72 from a selected position. The mounting base 72 can also have any other suitable configuration, for example, a ceiling mount, fixed floor/pedestal mount, a wall mount, or any other suitable mounting surface.

The support linkage 74 is operable to selectively position and/or orient the orienting platform 76 relative to the mounting base 72. The support linkage 74 includes a column base 86, a translatable column member 88, a shoulder joint 90, a boom base member 92, a boom first stage member 94, a boom second stage member 96, and a wrist joint 98. The column base 86 is fixedly attached to the mounting base 72. The translatable column member 88 is slideably coupled to the column base 86 for translation relative to column base 86. In many embodiments, the translatable column member 88 translates relative to the column base 86 along a vertically oriented axis. The boom base member 92 is rotationally coupled to the translatable column member 88 by the shoulder joint 90. The shoulder joint 90 is operable to selectively orient the boom base member 92 in a horizontal plane relative to the translatable column member 88, which has a fixed angular orientation relative to the column base 86 and the mounting base 72. The boom first stage member 94 is selectively translatable relative to the boom base member 92 in a horizontal direction, which in many embodiments is aligned with both the boom base member 92 and the boom first stage member 94. The boom second stage member 96 is likewise selectively translatable relative to the boom first stage member 94 in a horizontal direction, which in many embodiments is aligned with the boom first stage member 94 and the boom second stage member 96. Accordingly, the support linkage 74 is operable to selectively set the distance between the shoulder joint 90 and the distal end of the boom second stage member 96. The wrist joint 98 rotationally couples the distal end of the boom second stage member 96 to the orienting platform 76. The wrist joint 98 is operable to selectively set the angular orientation of the orienting platform 76 relative to the mounting base 72.

Each of the set-up linkages 78, 80 is operable to selectively position and/or orient the associated manipulator 82 relative to the orienting platform 76. Each of the set-up linkages 78, 80 includes a set-up linkage base link 100, a set-up linkage extension link 102, a set-up linkage parallelogram linkage portion 104, a set-up linkage vertical link 106, a second set-up linkage joint 108, and a manipulator support link 110. In each of the set-up linkage base links 100 of the outer set-up linkages 78 can be selectively oriented relative to the orienting platform 76 via the operation of the a first set-up linkage joint 84. In the embodiment shown, each of the set-up linkage base links 100 of the inner set-up linkages 80 is fixedly attached to the orienting platform 76. Each of the inner set-up linkages 80 can also be rotationally attached to the orienting platform 76 similar to the outer set-up linkages via an additional first set-up linkage joints 84. Each of the set-up linkage extension links 102 is translatable relative to the associated set-up linkage base link 100 in a horizontal direction, which in many embodiments is aligned with the associated set-up linkage base link and the set-up linkage extension link 102. Each of the set-up linkage parallelogram linkage portions 104 configured and operable to selectively translate the set-up linkage vertical link 106 in a vertical direction while keeping the set-up linkage vertical link 106 vertically oriented. In example embodiments, each of the set-up linkage parallelogram linkage portions 104 includes a first parallelogram joint 112, a coupling link 114, and a second parallelogram 116. The first parallelogram joint 112 rotationally couples the coupling link 114 to the set-up linkage extension link 102. The second parallelogram joint 116 rotationally couples the set-up linkage vertical link 106 to the coupling link 114. The first parallelogram joint 112 is rotationally tied to the second parallelogram joint 116 such that rotation of the coupling link 114 relative to the set-up linkage extension link 102 is matched by a counteracting rotation of the set-up linkage vertical link 106 relative to the coupling link 114 so as to maintain the set-up linkage vertical link 106 vertically oriented while the set-up linkage vertical link 106 is selectively translated vertically. The second set-up linkage joint 108 is operable to selectively orient the manipulator support link 110 relative to the set-up linkage vertical link 106, thereby selectively orienting the associated attached manipulator 82 relative to the set-up linkage vertical link 106.

Figure 7:
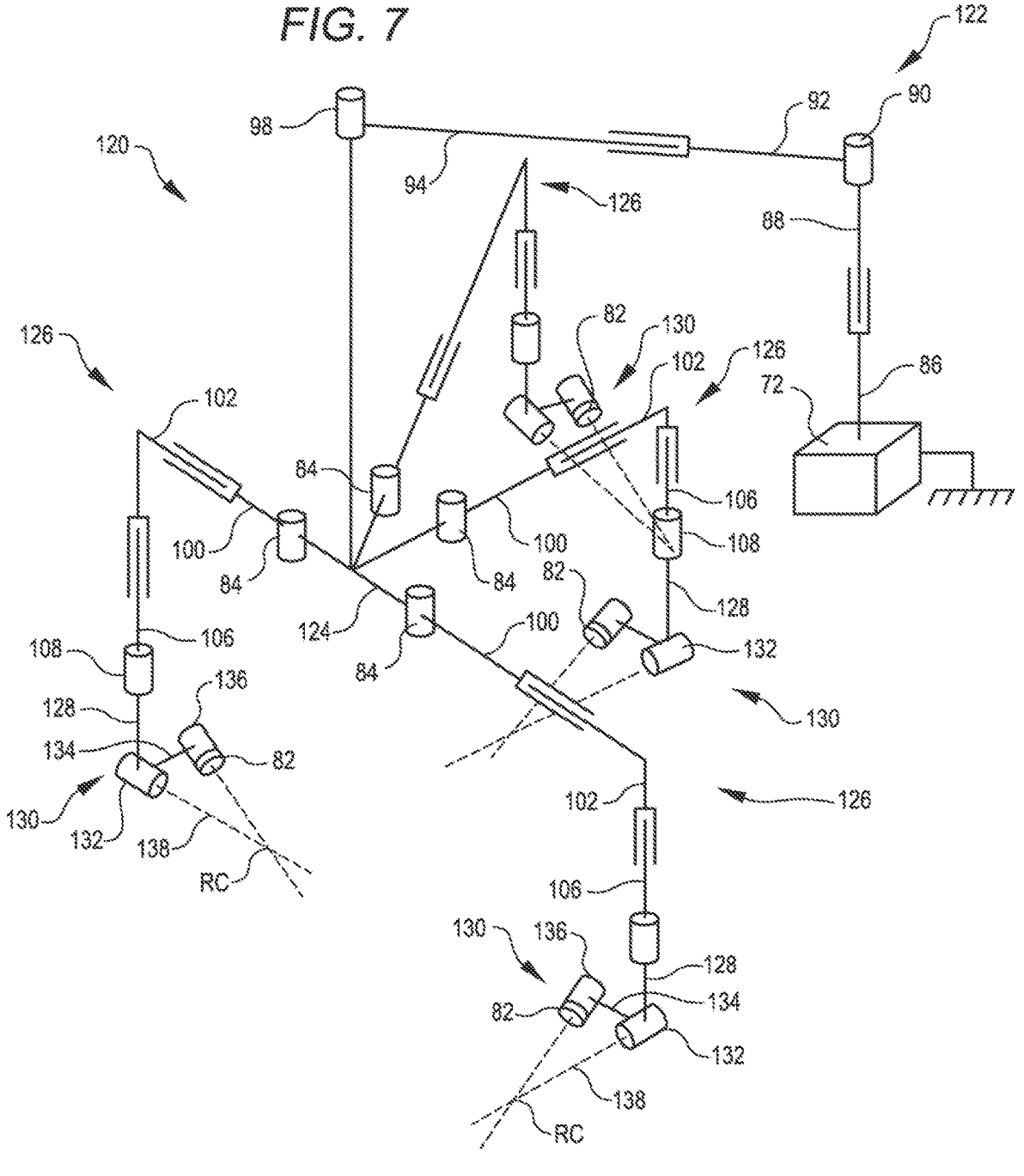
FIG. 7 is a perspective schematic representation of another robotic surgery system, in accordance with many embodiments.

FIG. 7 is a perspective schematic representation of a robotic surgery system 120, in accordance with many embodiments. Because the surgery system 120 includes components similar to components of the surgery system 70 of FIG. 6, the same reference numbers are used for similar components and the corresponding description of the similar components set forth above is applicable to the surgery system 120 and is omitted here to avoid repetition. The surgery system 120 includes the mounting base 72, a support linkage 122, an orienting platform 124, a plurality of set-up linkages 126 (four shown), and a plurality of the surgical instrument manipulators 82. Each of the manipulators 82 is operable to selectively articulate a surgical instrument mounted to the manipulator 82 and insertable into a patient along an insertion axis. Each of the manipulators 82 is attached to and supported by one of the set-up linkages 126. Each of the set-up linkages 126 is rotationally coupled to and supported by the orienting platform 124 by the first set-up linkage joint 84. The orienting platform 124 is rotationally coupled to and supported by the support linkage 122. And the support linkage 122 is fixedly attached to and supported by the mounting base 72.

The support linkage 122 is operable to selectively position and/or orient the orienting platform 124 relative to the mounting base 72. The support linkage 122 includes the column base 86, the translatable column member 88, the shoulder joint 90, the boom base member 92, the boom first stage member 94, and the wrist joint 98. The support linkage 122 is operable to selectively set the distance between the shoulder joint 90 and the distal end of the boom first stage member 94. The wrist joint 98 rotationally couples the distal end of the boom first stage member 94 to the orienting platform 124. The wrist joint 98 is operable to selectively set the angular orientation of the orienting platform 124 relative to the mounting base 72.

Each of the set-up linkages 126 is operable to selectively position and/or orient the associated manipulator 82 relative to the orienting platform 124. Each of the set-up linkages 126 includes the set-up linkage base link 100, the set-up linkage extension link 102, the set-up linkage vertical link 106, the second set-up linkage joint 108, a tornado mechanism support link 128, and a tornado mechanism 130. Each of the set-up linkage base links 100 of the set-up linkages 126 can be selectively oriented relative to the orienting platform 124 via the operation of the associated first set-up linkage joint 84. Each of the set-up linkage vertical links 106 is selectively translatable in a vertical direction relative to the associated set-up linkage extension link 102. The second set-up linkage joint 108 is operable to selectively orient the tornado mechanism support link 128 relative to the set-up linkage vertical link 106

Each of the tornado mechanisms 130 includes a tornado joint 132, a coupling link 134, and a manipulator support 136. The coupling link 134 fixedly couples the manipulator support 136 to the tornado joint 132. The tornado joint 130 is operable to rotate the manipulator support 136 relative to the tornado mechanism support link 128 around a tornado axis 136. The tornado mechanism 128 is configured to position and orient the manipulator support 134 such that the remote center of manipulation (RC) of the manipulator 82 is intersected by the tornado axis 136. Accordingly, operation of the tornado joint 132 can be used to reorient the associated manipulator 82 relative to the patient without moving the associated remote center of manipulation (RC) relative to the patient.

Figure 8:
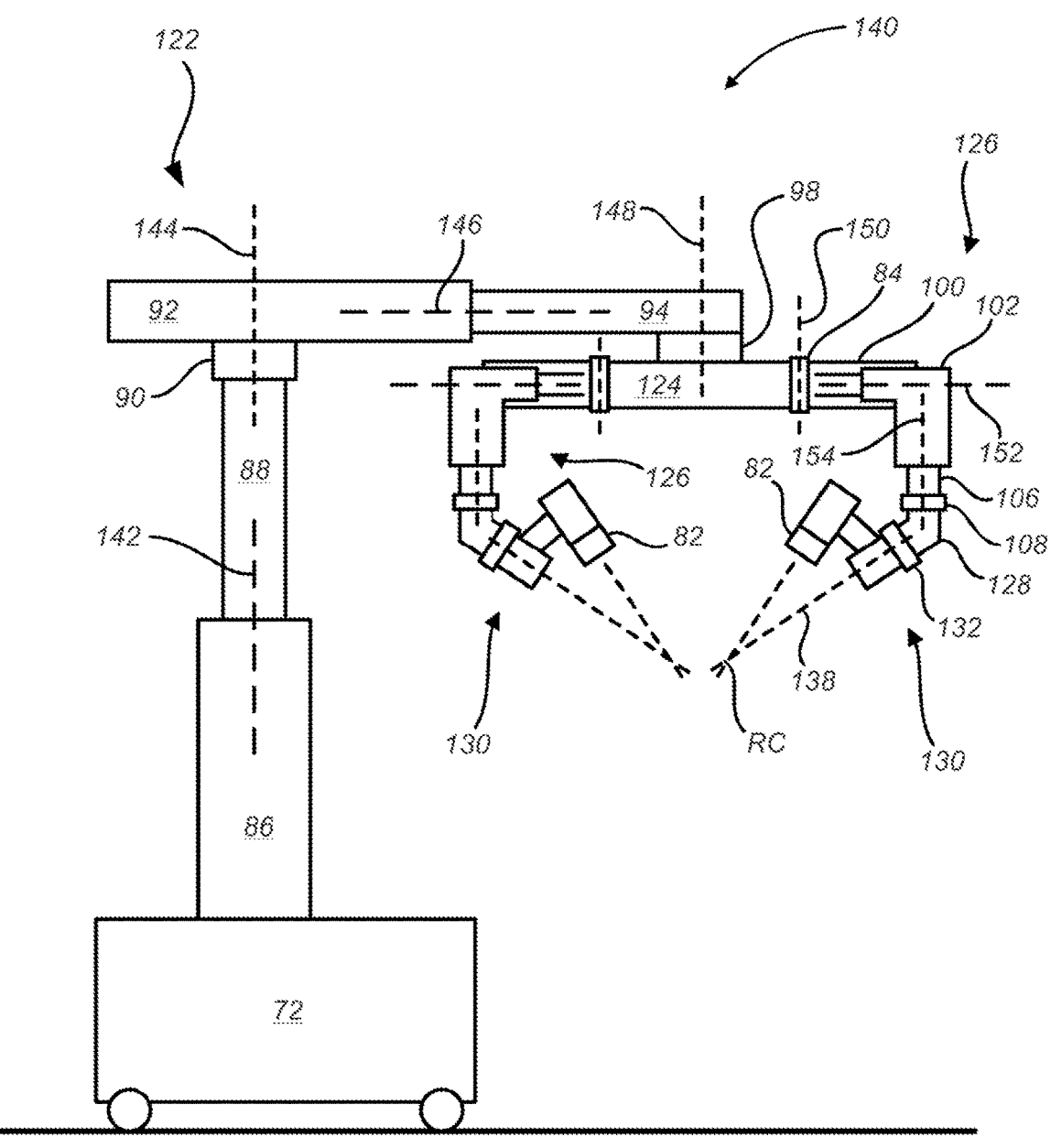
FIG. 8 shows a robotic surgery system, in accordance with many embodiments, in conformance with the schematic representation of FIG. 7.

FIG. 8 is a simplified representation of a robotic surgery system 140, in accordance with many embodiments, in conformance with the schematic representation of the robotic surgery system 120 of FIG. 7. Because the surgery system 140 conforms to the robotic surgery system 120 of FIG. 7, the same reference numbers are used for analogous components and the corresponding description of the analogous components set forth above is applicable to the surgery system 140 and is omitted here to avoid repetition.

The support linkage 122 is configured to selectively position and orient the orienting platform 124 relative to the mounting base 72 via relative movement between links of the support linkage 122 along multiple set-up structure axes. The translatable column member 88 is selectively repositionable relative to the column base 86 along a first set-up structure (SUS) axis 142, which is vertically oriented in many embodiments. The shoulder joint 90 is operable to selectively orient the boom base member 92 relative to the translatable column member 88 around a second SUS axis 144, which is vertically oriented in many embodiments. The boom first stage member 94 is selectively repositionable relative to the boom base member 92 along a third SUS axis 146, which is horizontally oriented in many embodiments. And the wrist joint 98 is operable to selectively orient the orienting platform 124 relative to the boom first stage member 94 around a fourth SUS axis 148, which is vertically oriented in many embodiments.

Each of the set-up linkages 126 is configured to selectively position and orient the associated manipulator 82 relative to the orienting platform 124 via relative movement between links of the set-up linkage 126 along multiple set-up joint (SUJ) axes. Each of the first set-up linkage joint 84 is operable to selectively orient the associated set-up linkage base link 100 relative to the orienting platform 124 around a first SUJ axis 150, which in many embodiments is vertically oriented. Each of the set-up linkage extension links 102 can be selectively repositioned relative to the associated set-up linkage base link 10 along a second SUJ axis 152, which is horizontally oriented in many embodiments. Each of the set-up linkage vertical links 106 can be selectively repositioned relative to the associated set-up linkage extension link 102 along a third SUJ axis 154, which is vertically oriented in many embodiments. Each of the second set-up linkage joints 108 is operable to selectively orient the tornado mechanism support link 128 relative to the set-up linkage vertical link 106 around the third SUJ axis 154. Each of the tornado joints 132 is operable to rotate the associated manipulator 82 around the associated tornado axis 138.

Figure 9:
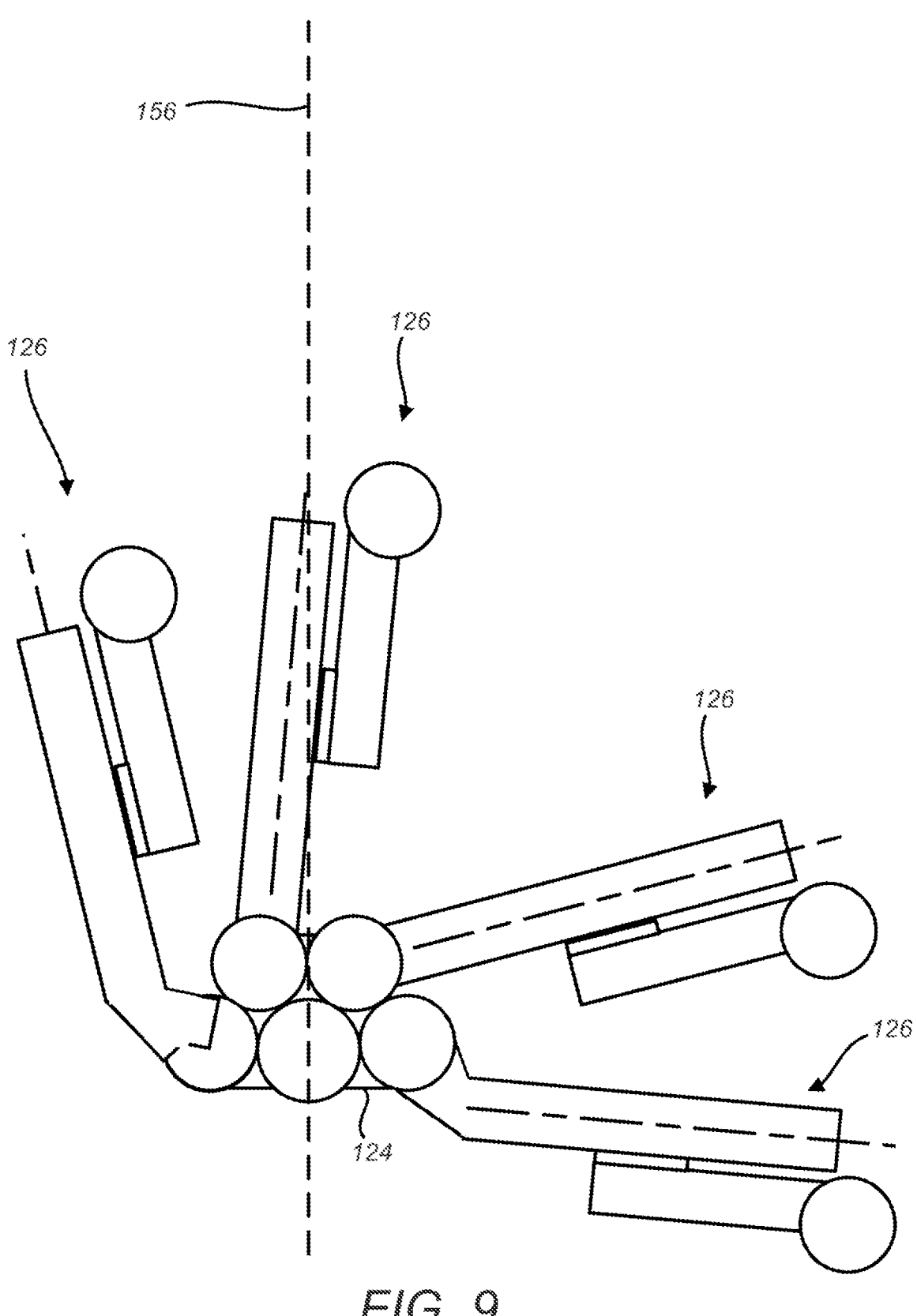
FIG. 9 illustrates rotational orientation limits of set-up linkages relative to an orienting platform of the robotic surgery system of FIG. 8.

FIG. 9 illustrates rotational orientation limits of the set-up linkages 126 relative to the orienting platform 124, in accordance with many embodiments. Each of the set-up linkages 126 is shown in a clockwise limit orientation relative to the orienting platform 124. A corresponding counter-clockwise limit orientation is represented by a mirror image of FIG. 9 relative to a vertically-oriented mirror plane. As illustrated, each of the two inner set-up linkages 126 can be oriented from 5 degrees from a vertical reference 156 in one direction to 75 degrees from the vertical reference 156 in the opposite direction. And as illustrated, each of the two outer set-up linkages can be oriented from 15 degrees to 95 degrees from the vertical reference 156 in a corresponding direction.

Figure 10:
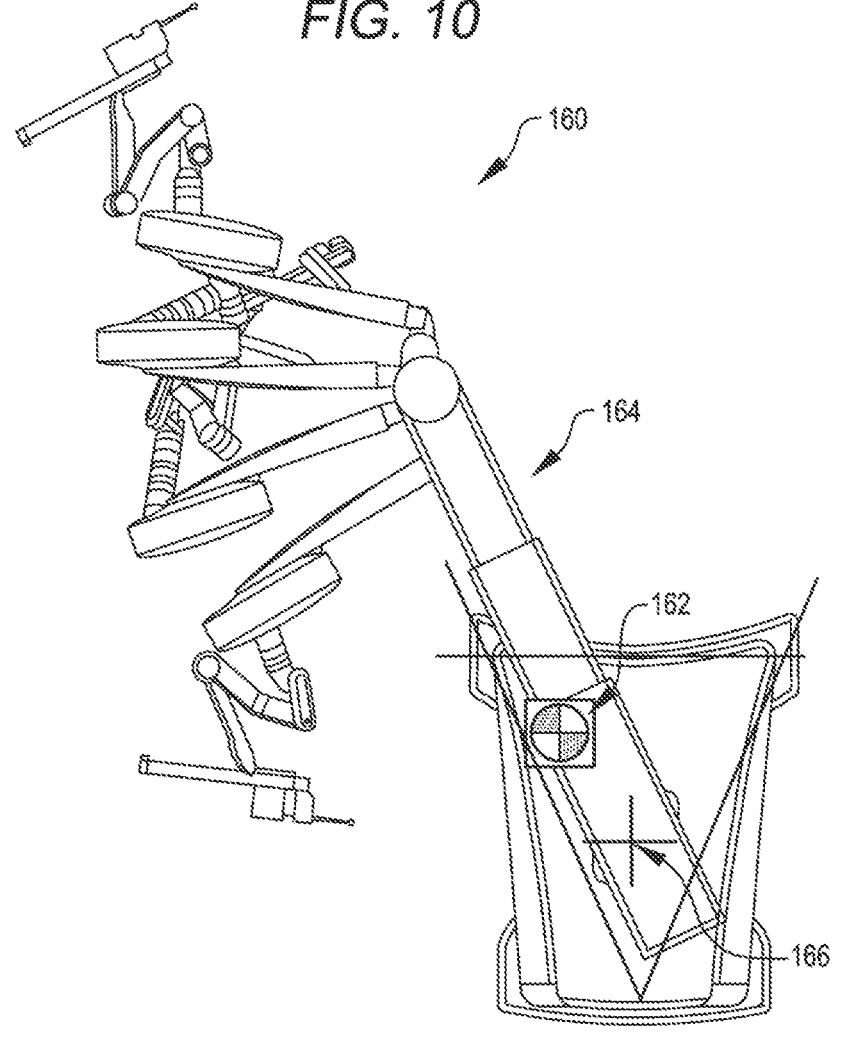
FIG. 10 shows a center of gravity diagram associated with a rotational limit of the boom assembly for a robotic surgery system, in accordance with many embodiments.

FIG. 10 shows a center of gravity diagram associated with a rotational limit of a support linkage for a robotic surgery system 160, in accordance with many embodiments. With components of the robotic surgery system 160 positioned and oriented to shift the center-of-gravity 162 of the robotic surgery system 160 to a maximum extent to one side relative to a support linkage 164 of the surgery system 160, a shoulder joint of the support linkage 164 can be configured to limit rotation of the support structure 164 around a set-up structure (SUS) shoulder-joint axis 166 to prevent exceeding a predetermined stability limit of the mounting base.

Figures 11A, 11B:
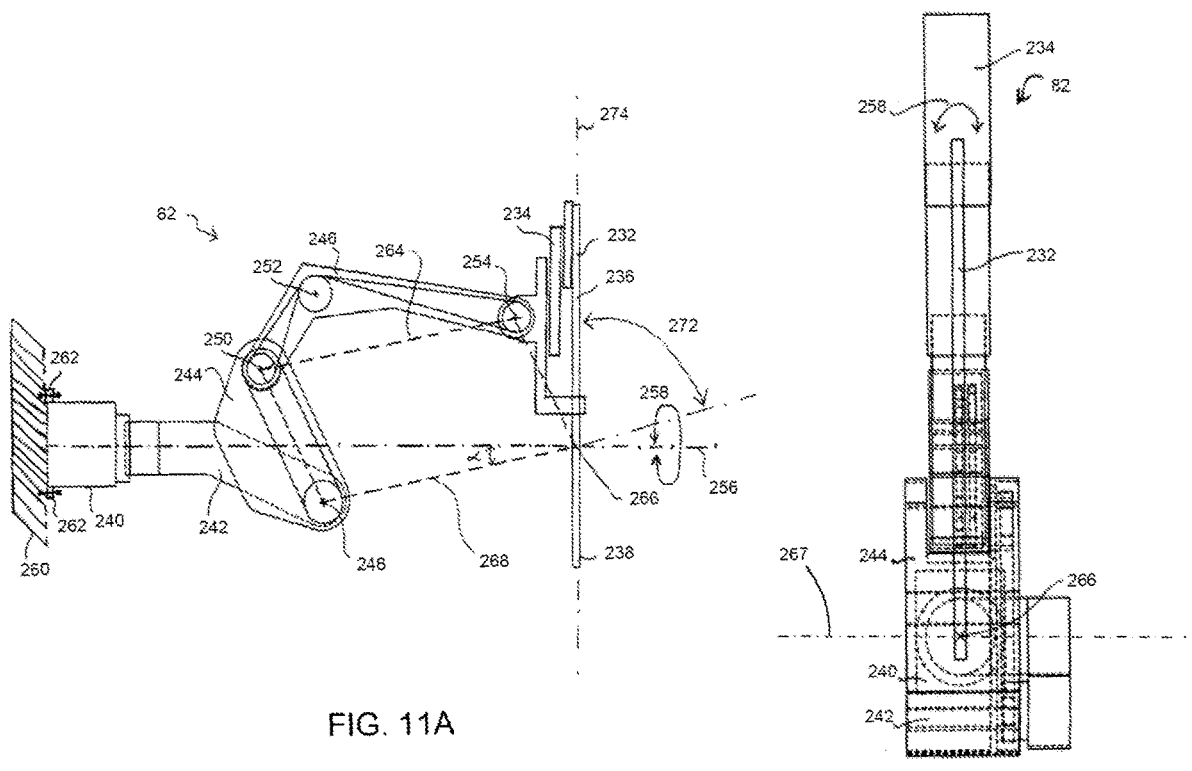
FIGS. 11A and 11B are side and front views, respectively, of an exemplary robotic manipulator linkage assembly constructed in accordance with the principles of the present invention.

Referring now to FIGS. 11A and 11B, side and front views are illustrated of an exemplary offset remote center robotic manipulator 82 constructed in accordance with the principles of the present invention. As described in greater detail below, the refined manipulator provides an offset remote center parallelogram manipulator linkage assembly which constrains a position of a surgical instrument 232 coupled to an instrument holder 234 during minimally invasive robotic surgery. The surgical instrument 232 includes an elongate shaft 236 having a distal working end 238 configured for insertion through an incision in a body wall into a body cavity of a patient. It will be appreciated that the above depictions are for illustrative purposes only and do not necessarily reflect the actual shape, size, or dimensions of the robotic surgical manipulator 82. This applies to all depictions hereinafter.

Generally, the offset remote center robotic manipulator 82 is configured to constrain shaft 236 motion relative to a center of rotation 266. As such, the shaft 236 is maintained substantially aligned through the center of rotation 266 as the shaft 236 is pivotally moved in at least one degree of freedom. Preferably, the center of rotation 266 is aligned with the incision point to the internal surgical site, for example, with a trocar or cannula at an abdominal wall during laparoscopic surgery. As such, an end effector of the surgical instrument 232 can be positioned safely by moving the proximal end of the shaft 236 using the offset remote center robotic manipulator 82 without imposing dangerous forces against the abdominal wall.

Referring back to FIG. 11A, the refined remote center manipulator generally includes an articulate linkage assembly 82 having a mounting base 240, a parallelogram linkage base 242, and a plurality of links 244, 246 and joints 248, 250, 252, 254. The term "joint" is used interchangeably with the term "pivot" herein. The mounting base 240 is rotationally coupled to the parallelogram linkage base 242 for rotation about a first axis 256, also known as the yaw axis, as indicated by arrow 258. The mounting base 240 allows for the surgical manipulator 82 to be mounted and supported by set-up arms/joints of a cart mount, ceiling mount, floor/pedestal mount, or other mounting surface. The mounting base 240 in this embodiment is fixed to base support 260 by screws or bolts 262, wherein the base support 260 is adapted to be attached to the set-up arms/joints. The parallelogram linkage base 242 is coupled to the instrument holder 234 by rigid links 244, 246 coupled together by rotational pivot joints 248, 250, 252, 254. The links 244, 246 and joints 248, 250, 252, 254 define a parallelogram 264 so as to constrain the elongate shaft 236 of the instrument 232 relative to the center of rotation 266 when the instrument 232 is mounted to the instrument holder 234 and the shaft 236 is moved along a plane of the parallelogram 264.

Significantly, the first axis 256 and the parallelogram 264 intersect the shaft 236 at the center of rotation 266, wherein the parallelogram 264 is angularly offset from the first axis 256. Specifically, a first side 268 which originates from the first pivot 248 of the parallelogram 264 adjacent the parallelogram linkage base 240 and the first axis 256 intersect the shaft 236 at the center of rotation 266, wherein the first side 268 and the first pivot 248 of the parallelogram 264 are angularly offset from the first axis 256. The first side 268 and first pivot 248 of the parallelogram 264 are offset from the first axis 256 by an angle a of at least 2 degrees, preferably by 10 degrees. Generally, the first side 268 and first pivot 248 of the parallelogram 264 are offset from the first axis 256 by angle a. in a range from about 2 degrees to about 45 degrees, preferably in a range from about 2 degrees to about 35 degrees.

Figure 12A:
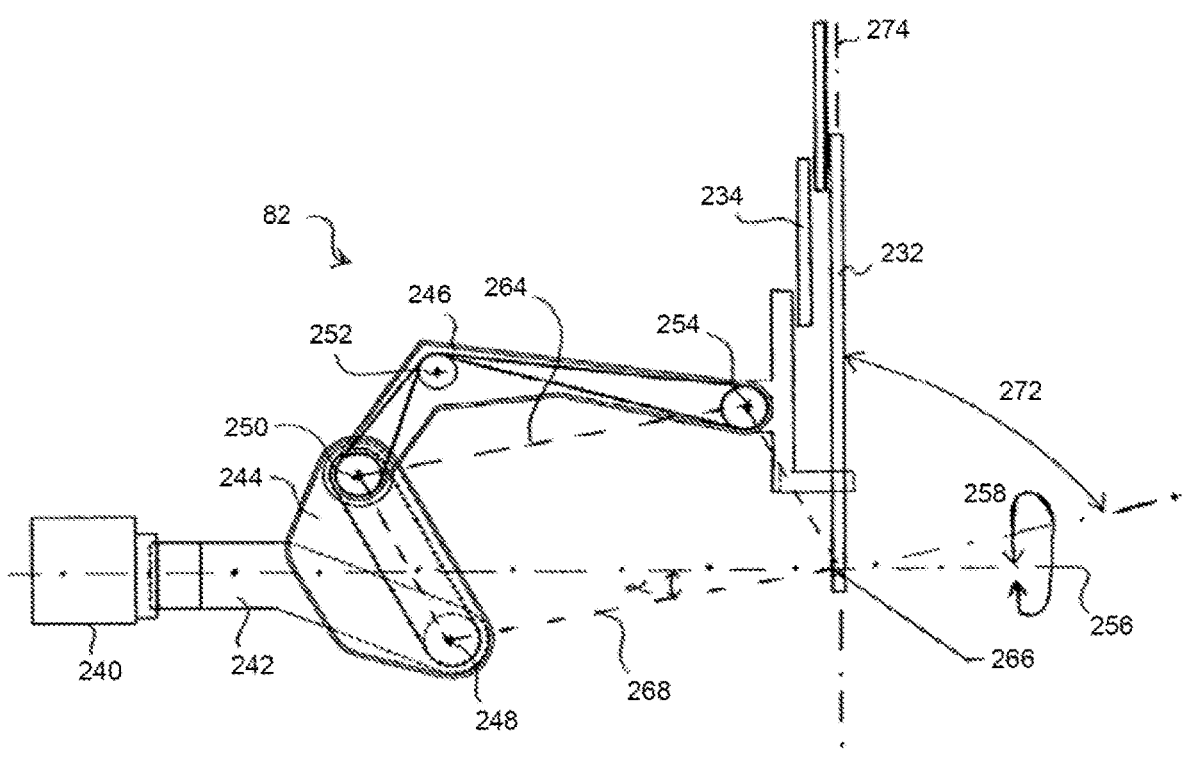
FIGS. 12A and 12B are additional side views of the exemplary robotic manipulator linkage assembly.
Figure 12B:
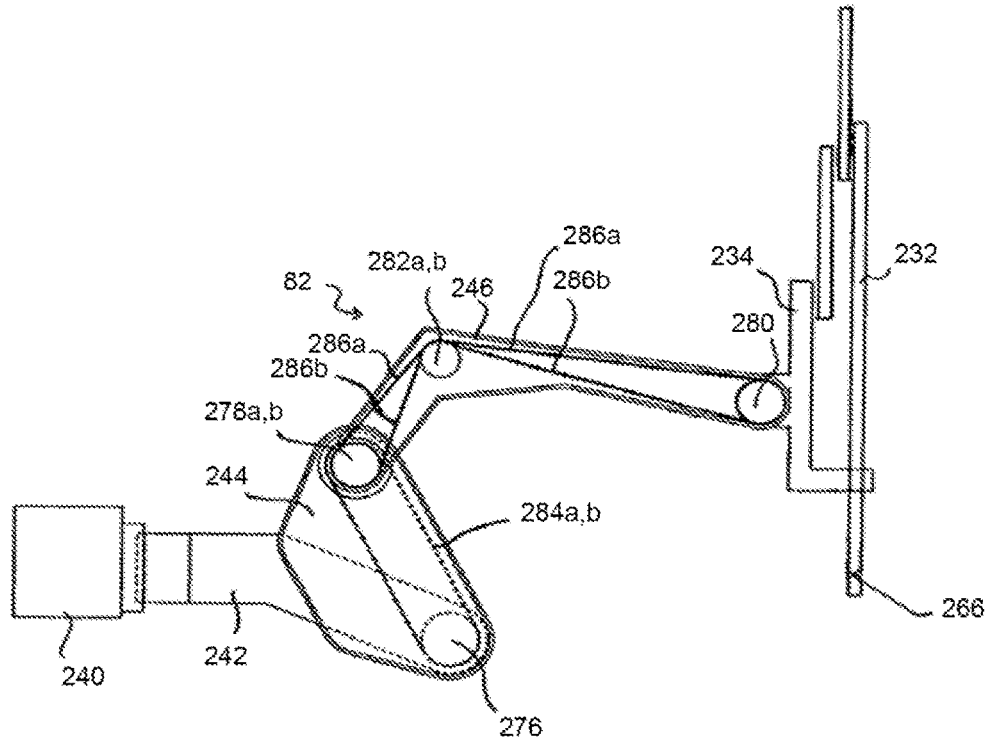
Figure 13A:
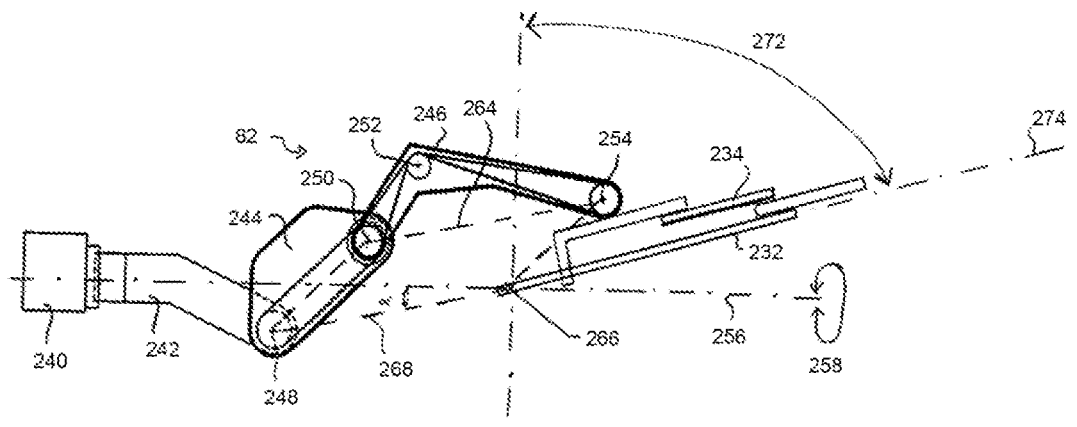
FIGS. 13A and 13B are side views of the exemplary robotic manipulator linkage assembly illustrating an improved range of motion along a pitch axis.
Figure 13B:
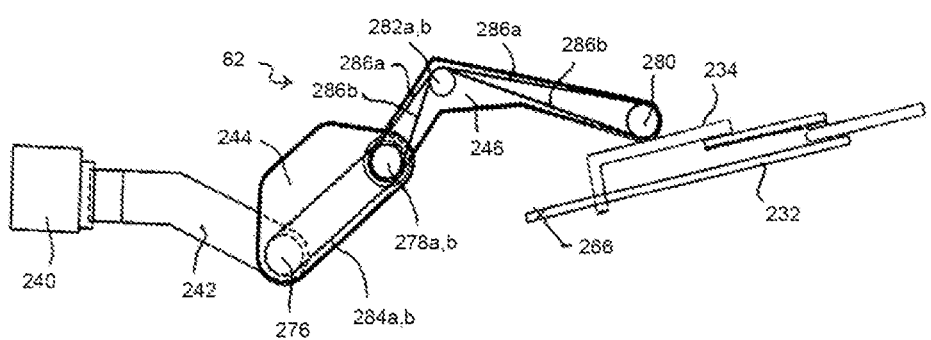

Referring now to FIGS. 12A and 12B, additional side views of the exemplary robotic manipulator linkage assembly 82 are illustrated showing the instrument holder 234 in an extended position. The offset parallelogram 264 arrangement allows for improved rotation of instrument 232 and holder 234 over the prior art while the remote center of rotation 266 remains at the same location. Specifically, as shown in FIGS. 13A, 13B, 14A, 14B, 15C and 15D, the offset articulate linkage assembly 82 provides an improved range of shaft 236 motion that is greater than ±55 degrees relative to a second axis 267 (which is perpendicular to the page in these illustrations and which passes through pivot point 266), preferably greater than ±60 degrees relative to the second axis 267. Generally, the offset articulate linkage assembly 82 constrains shaft 236 motion about pivot point 266 in a range from ±75 degrees relative to the second axis 267 as indicated by arrow 272, wherein the second axis 267 is sometimes referred to as a pitch axis. The manipulator 82 also provides an improved range of shaft 236 motion that is greater than ±90 degrees relative to the first axis 256, preferably greater than ±95 degrees relative to the first axis 256, as indicated by arrow 258 in FIGS. 15A and 15B. Typically, the cantilevered parallelogram linkage base 242 constrains shaft 236 motion about pivot point 266 in a range from ±168 degrees relative to the first axis 256.

Additionally, similar to the discussed prior art, the yaw axis 256, the pitch axis (which is perpendicular to the page), and an insertion axis 274 all intersect with each other at the remote center 266, which is aligned along a shaft 236 of the instrument 232. Thus, the instrument 232 can be pivotally rotated though desired angles as indicated by arrows 258 and 272 while the remote center of rotation 266 remains fixed in space relative to the mounting base 240 (mounting point to set-up arm) of manipulator 82. Hence, the entire manipulator 82 is generally moved to re-position the remote center 266. It will further be appreciated that the instrument 232 still has further driven degrees of freedom as supported by the offset remote center manipulator 82, including sliding motion of the instrument along the insertion axis 274.

The new and improved offset articulate linkage assembly 82 which decouples the first pivot 248 and first side 268 of the parallelogram 264 from the yaw axis 256 advantageously enhances the range of instrument 232 motion about pivot point 266 relative to the second axis 267, as indicated by arrow 272. The manipulator 82 further allows for an enhanced range of motion relative to the first axis 256, as indicated by arrow 258. An improved pivot range of motion along pitch and yaw axes in turn enhances the efficiency and ease of use of such robotic surgical systems. For example, the overall complexity of the robotic surgical system may be reduced due to the improved range of motion of the system. Specifically, the number of degrees of freedom in the set-up joints/arms may be reduced (e.g., less than six degrees of freedom). This allows for a simpler system platform requiring less pre-configuration of the set-up joints. As such, normal operating room personnel may rapidly arrange and prepare the robotic system for surgery with little or no specialized training.

Figure 14A:
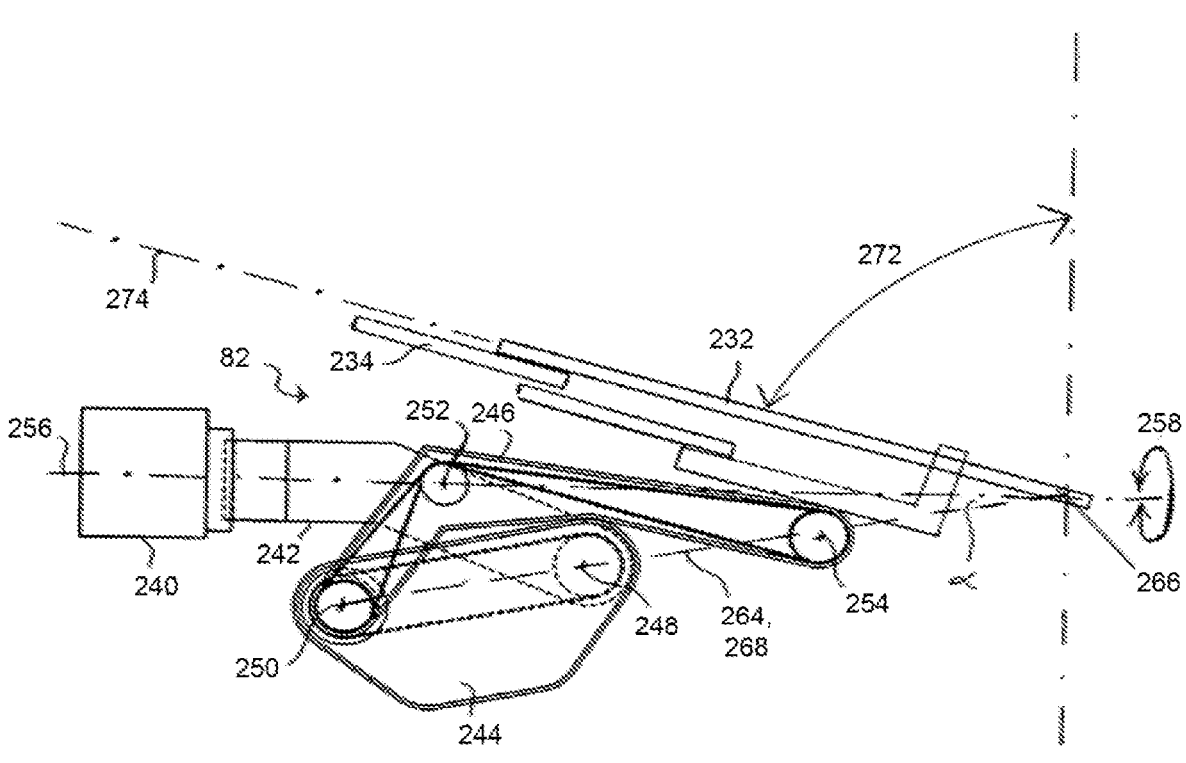
FIGS. 14A and 14B are side views of the exemplary robotic manipulator linkage assembly illustrating an improved range of motion along a pitch axis.
Figure 14B:
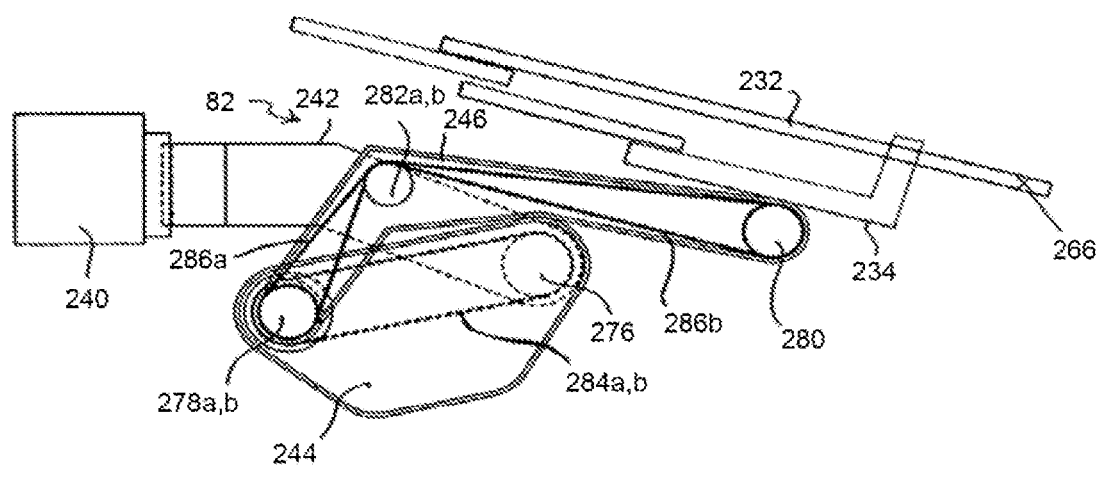
Figure 15A:
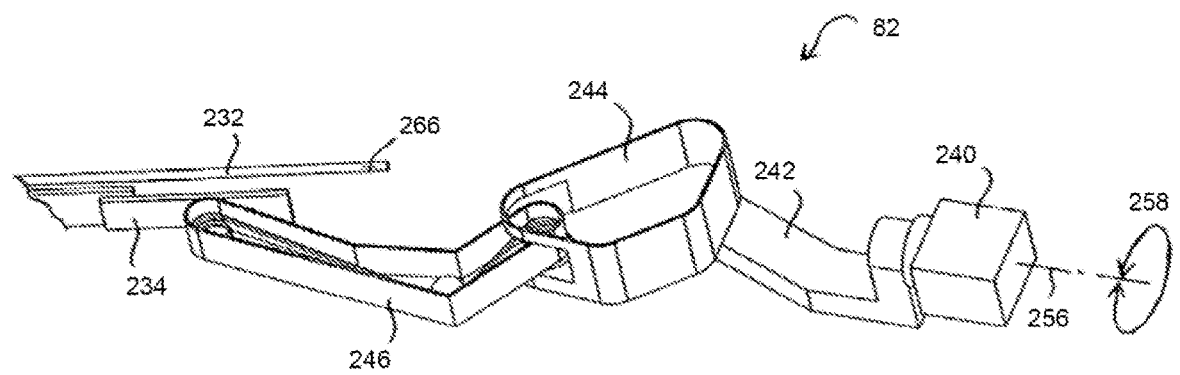
FIGS. 15A through 15D are perspective views of the exemplary robotic assembly manipulator linkage illustrating an improved range of motion along both the pitch and yaw axis.
Figure 15B:
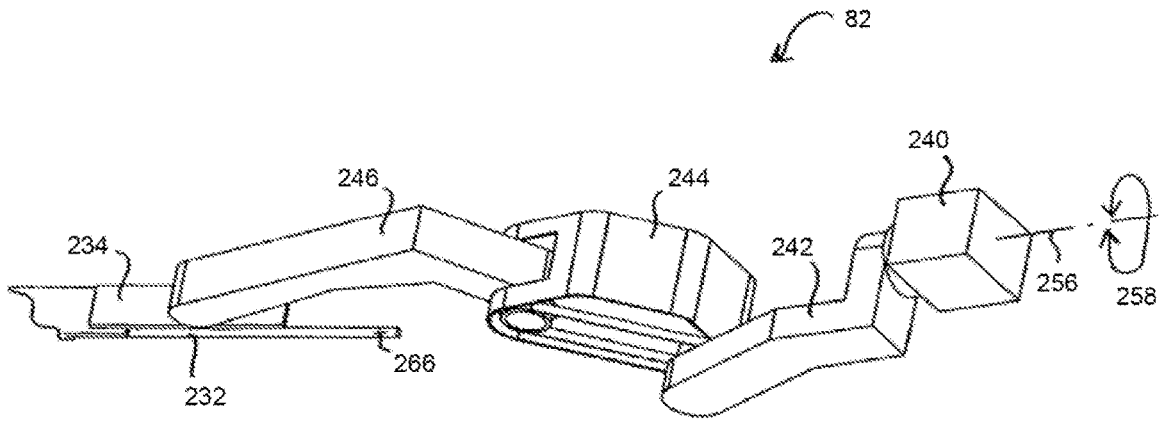
Figure 15C:
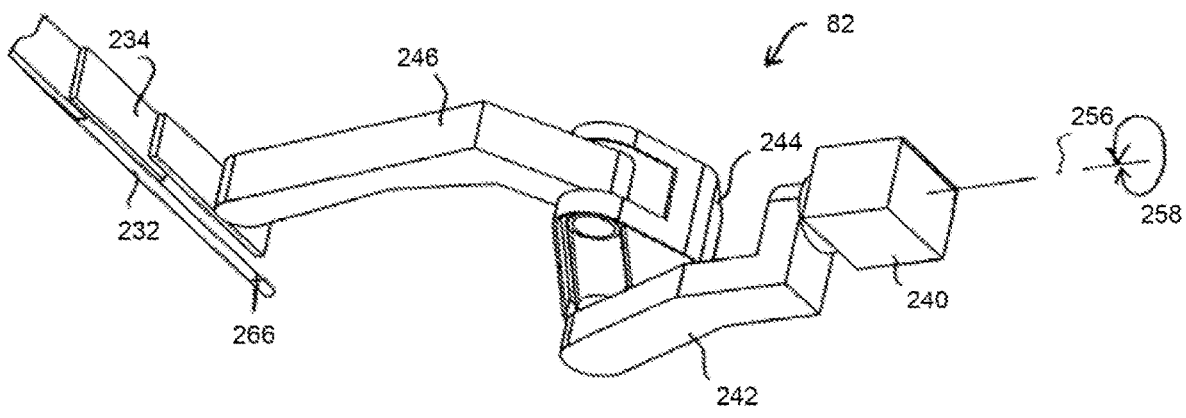
Figure 15D:
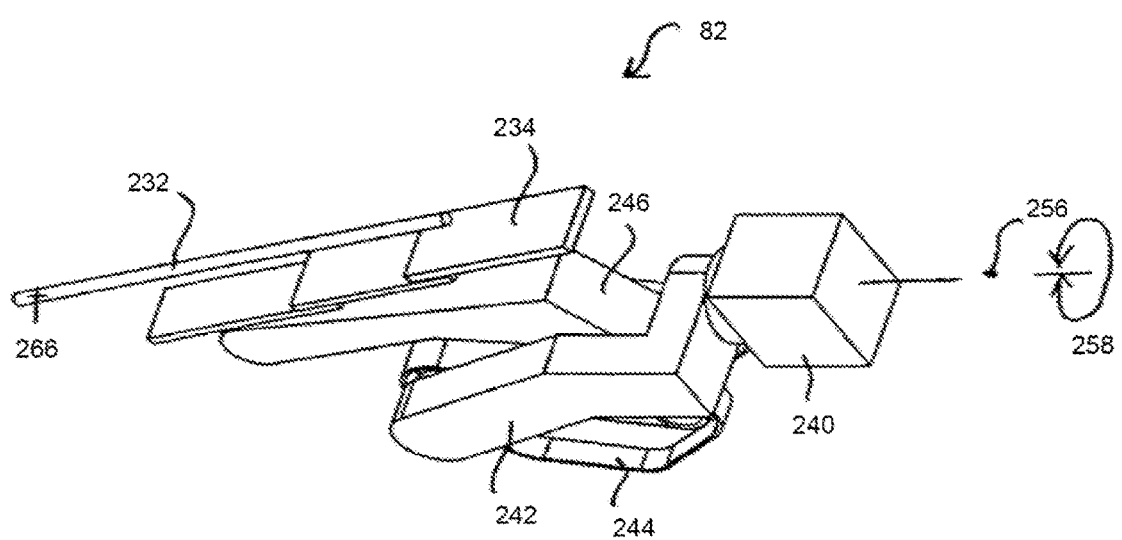

The plurality of links comprise an offset yaw link 242, a lowered vertical link 244, and a main bent link 246. The main link 246 is bent at an angle so as to provide clearance for the vertical link 244 to rest on the main bent link 246. This clearance prevents inter-linkage collisions between the vertical link 244 and the main bent link 246. For example, the main link 246 may be bent at an angle of about 22 degrees to allow clearance over a pitch dive 272 as shown in FIGS. 14A, 14B, and 15D. In such an embodiment, the main bent link 246 and the vertical link 244 as well as the instrument holder 234 are located in the same plane. It will be appreciated however that the main link 246 and the vertical link 244 may alternatively be offset in different planes (i.e., placed side by side) to reduce inter-linkage collisions in lieu of bending main link 246. The vertical link 244 pivot 248 is lower relative to the yaw axis 256 so as to provide the offset parallelogram 264 arrangement, as discussed above. The yaw link 242 is offset from links 244, 246, as best seen in FIGS. 15B through 15D. Link 242 and links 244, 246 are not in the same plane, but are rather offset side by side so as to reduce the possibility of interlinkage collisions between link 242 and links 244, 246.

At least one of the rigid links 242, 244, 246 coupled together by rotational pivot joints 248, 250, 252, 254 are not completely balanced in at least one degree of freedom. As such, a brake system may be coupled to the articulate linkage assembly 82. The brake system releasably inhibits articulation of at least one of the joints 248, 250, 252, 254. It will be appreciated that the offset remote center manipulator 82 may comprise a lighter system as the linkage is free of any counter-balancing weights. As such, the links 242, 244, 246 will preferably comprise sufficiently rigid and stiff structures so as to support any vibration issues associated with the lighter manipulator 82. It will further be appreciated that the offset remote center manipulator 82 may optionally be balanced by the use of weights, tension springs, gas springs, torsion springs, compression springs, air or hydraulic cylinders, torque motors, or combinations thereof.

Referring back to FIGS. 12B, 13B, and 14B, the offset remote center manipulator 82 may preferably comprise six pulleys 276, 278*a*, 278*b*, 280, 282*a*, 282*b* and four flexible elements 284*a*, 284*b*, 286*a*, 286*b* coupled to the pulleys 276, 278*a*, 278*b*, 280, 282*a*, 282*b* that are configured to constrain shaft 236 motion relative to the center of rotation 266. Links 242 and 246 are kept from rotating relative to each other by flexible elements 284*a*, 284*b* running on two pulleys 276, 278*a*, with one pulley 276 fixed to link 242 and one pulley 278*a* fixed to link 246. Links 244 and 234 are likewise kept from rotating relative to each other by a flexible elements 286*a*, 286*b* running on the remaining four pulleys 278*b*, 280, 282*a*, 282*b*, with one pulley 278*b* fixed to link 244, one pulley 280 fixed to link 234, and idler pulleys 282*a*, 282*b* to get the flexible elements 286*a*, 286*b* around the main bent link 246. Hence, links 242 and 246 can translate but not rotate relative to each other to maintain the parallelogram shape 264. Likewise, links 244 and 234 can translate but not rotate relative to each other to maintain the parallelogram shape 264. It will be appreciated that the term pulley 276, 278*a*, 278*b*, 280, 282*a*, 282*b* can include wheels, gears, sprockets, and the like.

The flexible element 284*a*, 284*b*, 286*a*, 286*b* may include belts, chains, or cables connected around the pulleys 276, 278*a*, 278*b*, 280, 282*a*, 282*b*. Preferably, the flexible elements comprise multi-layer metal belts, such as stainless steel belts having a breaking strength of approximately 800 lbs and being about a quarter inch wide. The belts are preferably multilayered utilizing at least 3 plies, preferably 5 plies to be strong enough to carry an adequate tension load yet sufficiently thin enough to not fatigue when repeatedly bent around the pulleys. Pulleys 276 and 278*a* have approximately the same diameter, e.g., 2.2 inches. Smaller pulleys 278*b* and 280 have approximately the same diameter, e.g., 1.8 inches. There are two idler pulleys 282*a*, 282*b* at the bend of the main link 246 to facilitate running of belts 286*a*, 286*b* in opposite directions so as to allow for attachment of the belts ends to be more robust. Utilization of non-continuous offset belts 284*a*, 284*b* and 286*a*, 286*b* provides for stress reduction, particularly at the attachment points, thus minimizing failures. Further, non-continuous belts allow for convenient tension and position adjustments. It will further be appreciated that belts 284*a*, 284*b* as well as belts 286*a*, 286*b* may optionally comprise continuous single belts. Additionally, the metal belts may be lightly coupled to flat flex cables that carry electrical signals along the manipulator arm.

The offset articulate linkage assembly 82 is driven by a series of motors. Motors may be located within the plurality of links to drive the pulley and belt mechanisms. Preferably, a majority of the motors are housed in the lowered vertical link 244. In particular, the motor which drives the pitch axis 272 rotating link 244 relative to link 242 through spur gears and a harmonic drive as well as the motors that run instrument actuation cables (e.g., wrist drive cables which may be spring tensioned) may be housed in link 244. Placement of the vertical link 244, the main bent link 246, and the instrument holder 234 in the same plane is advantageous as the motors that run the actuation cables are housed in link 244. Further, having the vertical link 244, the main bent link 246, and the instrument holder 234 in the same plane allows for space minimization at the distal end of the manipulator 82, which is of significant importance when performing minimally invasive robotic surgery in a confined operating environment. The motor driving the yaw axis 258 may be housed in mounting base 240.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

The invention claimed is:

1. A robotic surgery system comprising:
a mounting base;
a column base fixedly coupled with the mounting base;
a translatable column member slidably coupled to the column base for translation relative to the column base;
a boom assembly extending radially from the translatable column member, the boom assembly rotatably coupled with the translatable column member such that an angular orientation of the boom assembly relative to the translatable column member is adjustable;

an orienting platform coupled with the translatable column member via the boom assembly;

a first outer surgical instrument manipulator comprising a first outer manipulator mounting base and a first outer manipulator instrument holder, wherein the first outer surgical instrument manipulator is operable to selectively rotate the first outer manipulator instrument holder relative to the first outer manipulator mounting base around each of a first outer manipulator yaw axis and a first outer manipulator pitch axis, wherein each of the first outer manipulator yaw axis and the first outer manipulator pitch axis intersects a first remote center of manipulation, wherein the first outer manipulator pitch axis extends transverse to the first outer manipulator yaw axis, and wherein the first outer surgical instrument manipulator is operable to insert a first outer surgical instrument mounted to the first outer manipulator instrument holder along a first outer manipulator insertion axis into a patient through the first remote center of manipulation;

a second outer surgical instrument manipulator comprising a second outer manipulator mounting base and a second outer manipulator instrument holder, wherein the second outer surgical instrument manipulator is operable to selectively rotate the second outer manipulator instrument holder relative to the second outer manipulator mounting base around each of a second outer manipulator yaw axis and a second outer manipulator pitch axis, wherein each of the second outer manipulator yaw axis and the second outer manipulator pitch axis intersects a second remote center of manipulation, wherein the second outer manipulator pitch axis extends transverse to the second outer manipulator yaw axis, and wherein the second outer surgical instrument manipulator is operable to insert a second outer surgical instrument mounted to the second outer manipulator instrument holder along a second outer manipulator insertion axis into the patient through the second remote center of manipulation;

a first outer set-up linkage between the orienting platform and the first outer surgical instrument manipulator, the first outer set-up linkage configured to selectively position the first outer surgical instrument manipulator, wherein the first outer set-up linkage couples the first outer manipulator mounting base to the orienting platform, wherein the first outer set-up linkage is rotationally coupled to and supported by the orienting platform via a first outer set-up linkage first joint that is disposed at a first fixed location relative to the orienting platform, wherein the first outer manipulator mounting base is coupled with and supported by the first outer set-up linkage, wherein the first outer set-up linkage comprises a first outer set-up linkage extension link, a first outer set-up linkage coupling link, and a first outer set-up linkage second joint that couples the first outer set-up linkage coupling link to the first outer set-up linkage extension link, and wherein the first outer set-up linkage second joint is operable to rotate the first outer set-up linkage coupling link and the first outer manipulator mounting base relative to the first outer set-up linkage extension link around a first outer set-up linkage horizontally oriented axis; and a second outer set-up linkage between the orienting platform and the second outer surgical instrument manipulator, the second outer set-up linkage configured to selectively position the second outer surgical instrument manipulator, wherein the second outer set-up linkage couples the second outer manipulator mounting base to the orienting platform, wherein the second outer set-up linkage is rotationally coupled to and supported by the orienting platform via a second outer set-up linkage first joint that is disposed at a second fixed location relative to the orienting platform, wherein the second outer set-up linkage first joint is fixedly offset from the first outer set-up linkage first joint, wherein the second outer manipulator mounting base is coupled with and supported by the second outer set-up linkage, wherein the second outer set-up linkage comprises a second outer set-up linkage extension link, a second outer set-up linkage coupling link, and a second outer set-up linkage second joint that couples the second outer set-up linkage coupling link to the second outer set-up linkage extension link, and wherein the second outer set-up linkage second joint is operable to rotate the second outer set-up linkage coupling link and the second outer manipulator mounting base relative to the second outer set-up linkage extension link around a second outer set-up linkage horizontally oriented axis.

2. The robotic surgery system of claim 1, wherein the mounting base is movable and floor supported.

3. The robotic surgery system of claim 1, wherein the translatable column member is selectively positionable relative to the mounting base along a first axis that is vertically oriented.

4. The robotic surgery system of claim 1, wherein:

the first outer set-up linkage first joint is operable to rotate the first outer set-up linkage relative to the orienting platform around a first vertically oriented axis; and the second outer set-up linkage first joint is operable to rotate the second outer set-up linkage relative to the orienting platform around a second vertically oriented axis.

5. The robotic surgery system of claim 1, further comprising an inner set-up linkage and an inner surgical instrument manipulator, wherein:

the inner surgical instrument manipulator is coupled with the orienting platform via the inner set-up linkage;

the inner set-up linkage is coupled with the orienting platform between the first outer set-up linkage and the second outer set-up linkage;

the inner set-up linkage is coupled to and supported by the orienting platform;

the inner set-up linkage comprises an inner set-up linkage extension link, an inner set-up linkage coupling link, and an inner-setup linkage joint that couples the inner set-up linkage coupling link to the inner set-up linkage extension link and is operable to rotate the inner set-up linkage coupling link relative to the inner set-up linkage extension link around an inner set-up linkage horizontally oriented axis; and the inner surgical instrument manipulator is operable to selectively articulate an inner surgical instrument mounted to the inner surgical instrument manipulator and insert the inner surgical instrument along an inner manipulator insertion axis into the patient through an inner manipulator remote center of manipulation.

6. The robotic surgery system of claim 5, wherein:

the inner surgical instrument manipulator comprises an inner manipulator instrument holder to which the inner surgical instrument is mounted;

the inner surgical instrument manipulator is operable to rotate the inner manipulator instrument holder around an inner manipulator yaw axis that intersects the inner manipulator remote center of manipulation;

the inner surgical instrument manipulator is operable to rotate the inner manipulator instrument holder around an inner manipulator pitch axis that intersects the inner manipulator remote center of manipulation;

the inner manipulator yaw axis is transverse to the inner manipulator insertion axis;

the inner manipulator pitch axis is transverse to the inner manipulator insertion axis; and the inner manipulator pitch axis is transverse to the inner manipulator yaw axis.

7. The robotic surgery system of claim 5, further comprising a second inner set-up linkage and a second inner surgical instrument manipulator coupled with the orienting platform via the second inner set-up linkage, wherein:

the second inner set-up linkage is coupled to and supported by the orienting platform between the first outer set-up linkage and the second outer set-up linkage;

the second inner set-up linkage comprises a second inner set-up linkage extension link, a second inner linkage coupling link, and a second inner linkage joint that couples the second inner linkage coupling link to the second inner set-up linkage extension link and is operable to rotate the second inner linkage coupling link relative to the second inner set-up linkage extension link around a second inner set-up linkage horizontally oriented axis; and the second inner surgical instrument manipulator is operable to selectively articulate a second inner surgical instrument mounted to the second inner surgical instrument manipulator and to insert the second inner surgical instrument along a second inner manipulator insertion axis into the patient through a second inner manipulator remote center of manipulation.

8. The robotic surgery system of claim 7, wherein:

the second inner surgical instrument manipulator comprises a second inner manipulator instrument holder to which the second inner surgical instrument is mountable;

the second inner surgical instrument manipulator is operable to rotate the second inner manipulator instrument holder around a second inner manipulator yaw axis that intersects the second inner manipulator remote center of manipulation;

the second inner surgical instrument manipulator is operable to rotate the second inner-manipulator instrument holder around a second inner manipulator pitch axis that intersects the second inner manipulator remote center of manipulation;

the second inner manipulator yaw axis is transverse to the second inner manipulator insertion axis;

the second inner manipulator pitch axis is transverse to the second inner manipulator insertion axis; and the second inner manipulator pitch axis is transverse to the second inner manipulator yaw axis.

9. The robotic surgery system of claim 8, wherein:

the first outer set-up linkage further comprise a first outer set-up linkage base link;

the first outer set-up linkage extension link is slidably coupled with the first outer set-up linkage base link for horizontal translation of the first outer set-up linkage extension link relative to the first outer set-up linkage base link;

the second outer set-up linkage further comprise a second outer set-up linkage base link; and the second outer set-up linkage extension link is slidably coupled with the second outer set-up linkage base link for horizontal translation of the second outer set-up linkage extension link relative to the second outer set-up linkage base link.

10. The robotic surgery system of claim 9, wherein:

the inner set-up linkage further comprise an inner set-up linkage base link;

the inner set-up linkage extension link is slidably coupled with the inner set-up linkage base link for horizontal translation of the inner set-up linkage extension link relative to the inner set-up linkage base link;

the second inner set-up linkage further comprise a second inner set-up linkage base link; and the second inner set-up linkage extension link is slidably coupled with the second inner set-up linkage base link for horizontal translation of the second inner set-up linkage extension link relative to the second inner set-up linkage base link.

11. The robotic surgery system of claim 1, wherein:

the first outer set-up linkage and the first outer surgical instrument manipulator are located at a first outer side of the robotic surgery system; and the second outer set-up linkage and the second outer surgical instrument manipulator are located at a second outer side of the robotic surgery system, wherein the second outer side is disposed opposite to the first outer side.

12. The robotic surgery system of claim 1, wherein the boom assembly is operable to change a distance between the orienting platform and the translatable column.

13. The robotic surgery system of claim 1, further comprising a shoulder joint rotatably coupling the boom assembly with the translatable column member, wherein the shoulder joint is operable to adjust the angular orientation of the boom assembly relative to the translatable column member.

14. The robotic surgery system of claim 13, further comprising a wrist joint coupling the orienting platform with the boom assembly, wherein the wrist joint is operable to reorient the orienting platform relative to the boom assembly.

15. The robotic surgery system of claim 1, further comprising a wrist joint coupled with the translatable column member, wherein:

the orienting platform is coupled with the translatable column member via the wrist joint; and the wrist joint is operable to selectively set an angular orientation of the orienting platform relative to the mounting base.

16. The robotic surgery system of claim 15, wherein the orienting platform, the first outer set-up linkage first joint, and the second outer set-up linkage first joint are configured and coupled so that the wrist joint is operable to simultaneously reorient the first outer set-up linkage first joint and the second outer set-up linkage first joint relative to the mounting base.

17. The robotic surgery system of claim 1, wherein adjustment of the angular orientation of the boom assembly relative to the translatable column member adjusts an angular orientation of the orienting platform together with the first and second outer set-up linkages relative to the translatable column member.

* * * * *